US009646599B2

(12) United States Patent
Gayle et al.

(10) Patent No.: US 9,646,599 B2
(45) Date of Patent: May 9, 2017

(54) REMOLDABLE CONTOUR SENSOR HOLDER

(71) Applicant: Spirit AeroSystems, Inc., Wichita, KS (US)

(72) Inventors: David Michael Gayle, Andover, KS (US); Adam Joseph Donar, Wichita, KS (US); Nicholas John Pilla, Wichita, KS (US)

(73) Assignee: Spirit AeroSystems, Inc., Wichita, KS (US)

( * ) Notice: Subject to any disclaimer, the term of this patent is extended or adjusted under 35 U.S.C. 154(b) by 482 days.

(21) Appl. No.: 14/062,532

(22) Filed: Oct. 24, 2013

(65) Prior Publication Data

US 2015/0114143 A1    Apr. 30, 2015

(51) Int. Cl.
  *G01N 29/04*  (2006.01)
  *G01N 29/28*  (2006.01)
  *G10K 11/24*  (2006.01)
  *G01N 29/27*  (2006.01)

(52) U.S. Cl.
  CPC ........... *G10K 11/24* (2013.01); *G01N 29/043* (2013.01); *G01N 29/27* (2013.01); *G01N 29/28* (2013.01); *G01N 2291/2638* (2013.01)

(58) Field of Classification Search
  CPC .. G01N 27/902; G01N 29/28; G01N 27/9033; G01N 29/223; G01N 29/221; G01N 29/2456
  See application file for complete search history.

(56) References Cited

U.S. PATENT DOCUMENTS

| 3,497,728 | A | * | 2/1970 | Ostrofsky | ............... | G01B 17/02 |
| | | | | | | 310/336 |
| 4,719,422 | A | * | 1/1988 | deWalle | ............. | G01N 27/9033 |
| | | | | | | 324/234 |
| 4,977,780 | A | * | 12/1990 | Machida | ................ | G10K 11/02 |
| | | | | | | 600/459 |
| 5,155,878 | A | * | 10/1992 | Dellis | .................... | B25G 1/102 |
| | | | | | | 16/421 |
| 5,176,140 | A | * | 1/1993 | Kami | ........................ | A61B 8/12 |
| | | | | | | 310/327 |
| 5,278,498 | A | * | 1/1994 | Vernon | ................ | G01N 27/902 |
| | | | | | | 324/234 |

(Continued)

FOREIGN PATENT DOCUMENTS

JP      04235343 A  *  8/1992
JP      04238208 A  *  8/1992

(Continued)

OTHER PUBLICATIONS

Eddy Current test probe assembly, available on the internet at http://ecitende.com/products, Aug. 3, 2011.*

*Primary Examiner* — David A Rogers
(74) *Attorney, Agent, or Firm* — Hovey Williams LLP

(57) ABSTRACT

A sensor assembly for inspecting a part, the sensor assembly comprising a sensor for sensing a defect of the part and a remoldable housing for retaining and positioning the sensor in alignment with the defect of the part. The housing is formed of a moldable material and may be molded into a shape that conforms to a contour of the part when a stimulus is applied to the housing and may harden into the shape when the stimulus is removed from the housing.

13 Claims, 3 Drawing Sheets

(56) References Cited

U.S. PATENT DOCUMENTS

| | | | | |
|---|---|---|---|---|
| H1290 H * | 2/1994 | Mann | | G10K 11/02 |
| | | | | 310/336 |
| 5,426,980 A * | 6/1995 | Smith | | G01N 29/069 |
| | | | | 73/632 |
| 5,754,166 A * | 5/1998 | Baba | | G05G 1/10 |
| | | | | 341/22 |
| 5,759,090 A * | 6/1998 | Kawate | | B24B 19/26 |
| | | | | 451/28 |
| 5,806,664 A * | 9/1998 | Hartman | | H01H 9/02 |
| | | | | 200/329 |
| 5,829,171 A * | 11/1998 | Weber | | A43B 7/28 |
| | | | | 36/2.6 |
| 5,841,277 A * | 11/1998 | Hedengren | | G01N 27/902 |
| | | | | 324/237 |
| 5,997,481 A * | 12/1999 | Adams | | A61B 8/4281 |
| | | | | 600/459 |
| 6,156,842 A * | 12/2000 | Hoenig | | C08L 23/08 |
| | | | | 428/373 |
| 6,160,084 A * | 12/2000 | Langer | | A61L 27/18 |
| | | | | 528/176 |
| 6,198,280 B1 * | 3/2001 | Hensley | | G01N 27/902 |
| | | | | 324/225 |
| 6,234,025 B1 * | 5/2001 | Gieske | | G01N 29/221 |
| | | | | 73/629 |
| 6,288,537 B1 * | 9/2001 | Viertl | | G01N 27/904 |
| | | | | 324/229 |
| 6,469,503 B2 * | 10/2002 | Trantow | | G01N 27/9033 |
| | | | | 324/219 |
| 6,812,697 B2 * | 11/2004 | McKnight | | G01N 27/9006 |
| | | | | 324/242 |
| 7,352,176 B1 * | 4/2008 | Roach | | G01N 27/9033 |
| | | | | 324/228 |
| 7,670,302 B2 * | 3/2010 | Griffin | | A61L 31/022 |
| | | | | 600/585 |
| 7,767,939 B2 * | 8/2010 | Ferguson | | A01M 1/2077 |
| | | | | 219/219 |
| 7,987,721 B2 * | 8/2011 | Schulz | | G01N 29/11 |
| | | | | 73/620 |
| 8,013,599 B2 * | 9/2011 | Suh | | G01B 7/28 |
| | | | | 324/232 |
| 8,127,612 B2 * | 3/2012 | Mitchell | | G01N 29/07 |
| | | | | 73/623 |
| 8,166,823 B2 * | 5/2012 | Lam | | G01N 29/221 |
| | | | | 73/600 |
| 8,510,924 B2 * | 8/2013 | Mankame | | B23Q 3/086 |
| | | | | 264/230 |
| 8,674,940 B2 * | 3/2014 | Jameson | | G05G 9/047 |
| | | | | 345/156 |
| 8,758,268 B2 * | 6/2014 | Bown | | A61M 25/09 |
| | | | | 148/563 |
| 8,784,465 B2 * | 7/2014 | Sahatjian | | A61F 2/88 |
| | | | | 264/305 |
| 2004/0056656 A1 * | 3/2004 | McKnight | | G01N 27/9006 |
| | | | | 324/262 |
| 2005/0206374 A1 * | 9/2005 | Roney | | G01N 27/902 |
| | | | | 324/242 |
| 2008/0188753 A1 * | 8/2008 | Chang | | B06B 1/0292 |
| | | | | 600/459 |
| 2008/0224881 A1 * | 9/2008 | Eaton | | G01S 7/4813 |
| | | | | 340/686.6 |
| 2009/0115410 A1 * | 5/2009 | McKnight | | G01N 27/904 |
| | | | | 324/240 |
| 2009/0218321 A1 * | 9/2009 | Ashman | | A61B 17/00 |
| | | | | 219/50 |
| 2010/0125207 A1 * | 5/2010 | Kim | | A61B 8/4209 |
| | | | | 600/459 |
| 2011/0042380 A1 * | 2/2011 | Tsou | | B29B 9/06 |
| | | | | 220/495.06 |
| 2011/0089962 A1 * | 4/2011 | Pagani | | G01R 1/07 |
| | | | | 324/754.03 |
| 2011/0150037 A1 * | 6/2011 | Price | | G01K 1/083 |
| | | | | 374/209 |
| 2013/0199279 A1 * | 8/2013 | Boles | | G01N 27/9026 |
| | | | | 73/112.01 |
| 2014/0211826 A1 * | 7/2014 | Skurkis | | G01N 27/041 |
| | | | | 374/46 |
| 2014/0276224 A1 * | 9/2014 | Ranganathan | | A61B 5/6851 |
| | | | | 600/585 |
| 2014/0358008 A1 * | 12/2014 | Yoo | | A61B 8/4281 |
| | | | | 600/472 |

FOREIGN PATENT DOCUMENTS

| | | | | |
|---|---|---|---|---|
| JP | | 07163560 A * | 6/1995 | |
| WO | WO 2007044951 A2 * | 4/2007 | | A61F 7/007 |

* cited by examiner

REMOLDABLE CONTOUR SENSOR HOLDER

BACKGROUND

Embodiments of the present invention relate to modifiable sensor assemblies. More particularly, embodiments of the present invention relate to modifiable sensor assemblies having a modifiable housing for inspecting a part.

Manufactured parts often require nondestructive inspection to detect foreign particles or internal defects such as inclusions, porosity, cracks, or delamination. Nondestructive inspection techniques such as ultrasound use a sensor device that projects wave energy into the part and senses reflections of the wave energy bouncing off of internal defects in the part. Reflections from internal defects are detected as anomalies with respect to readings from surrounding areas. To obtain accurate readings, the sensor must be in a precise position relative to the part. To that end, the sensor is mounted in or attached to a housing or a shoe that conforms to a contour of the part and holds the sensor at the precise position.

To create the housing, it is first drawn using CAD software, formed using conventional methods such as milling, bending, and extrusion, and then tested against the part. If the part itself was not formed with tooling or other precise processes, significant contour irregularities will cause the housing to be misaligned. This requires the housing to be modified by sanding, grinding, etc. Creating and modifying the housing are cumbersome tasks that cannot be easily performed and virtually cannot be performed in the field. Also, a set of multiple housings often must be kept for different parts or contours. The set is difficult to transport and may result in a wrong housing being used, which results in erroneous inspection results.

Accordingly, there is a need for a sensor assembly that overcomes the above limitations.

SUMMARY

Embodiments of the present invention solve the above-mentioned problems and provide a distinct advance in the art of modifiable sensor assemblies. More particularly, the invention is useful for being modified to dimensionally match a part and align a sensor with the part during inspection without performing tedious reshaping procedures such as material sanding.

One embodiment of the invention provides a sensor assembly for inspecting a part. The assembly includes a sensor for sensing a defect of the part and a remoldable housing for retaining the sensor. The remoldable housing is formed of a material that may be molded into a shape that conforms to a contour of the part when a stimulus is applied to the housing and hardens into the shape when the stimulus is removed from the housing.

Another embodiment of the invention provides a sensor assembly including a sensor for sensing a defect of a part, a non-remoldable component forming an approximation of a contour of the part and housing the sensor, and a remoldable shim that may be molded into a shape that conforms to the approximation when a stimulus is applied thereto. The shim hardens into the shape when the stimulus is removed to maintain the sensor alignment for ensuring accurate sensor readings.

Another embodiment of the invention provides a method for inspecting a part. The method includes the steps of placing a sensor in a remoldable housing, applying a stimulus to the housing, molding the housing to conform to a contour of the part such that the sensor is at a position to transmit or receive a signal for sensing a defect of the part, detecting the signal, remolding the housing into a modified shape for repositioning the sensor in response to the signal received, and removing the stimulus to harden the housing into the modified shape.

This summary is provided to introduce a selection of concepts in a simplified form that are further described below in the detailed description. This summary is not intended to identify key contours or essential contours of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

Figure 1:
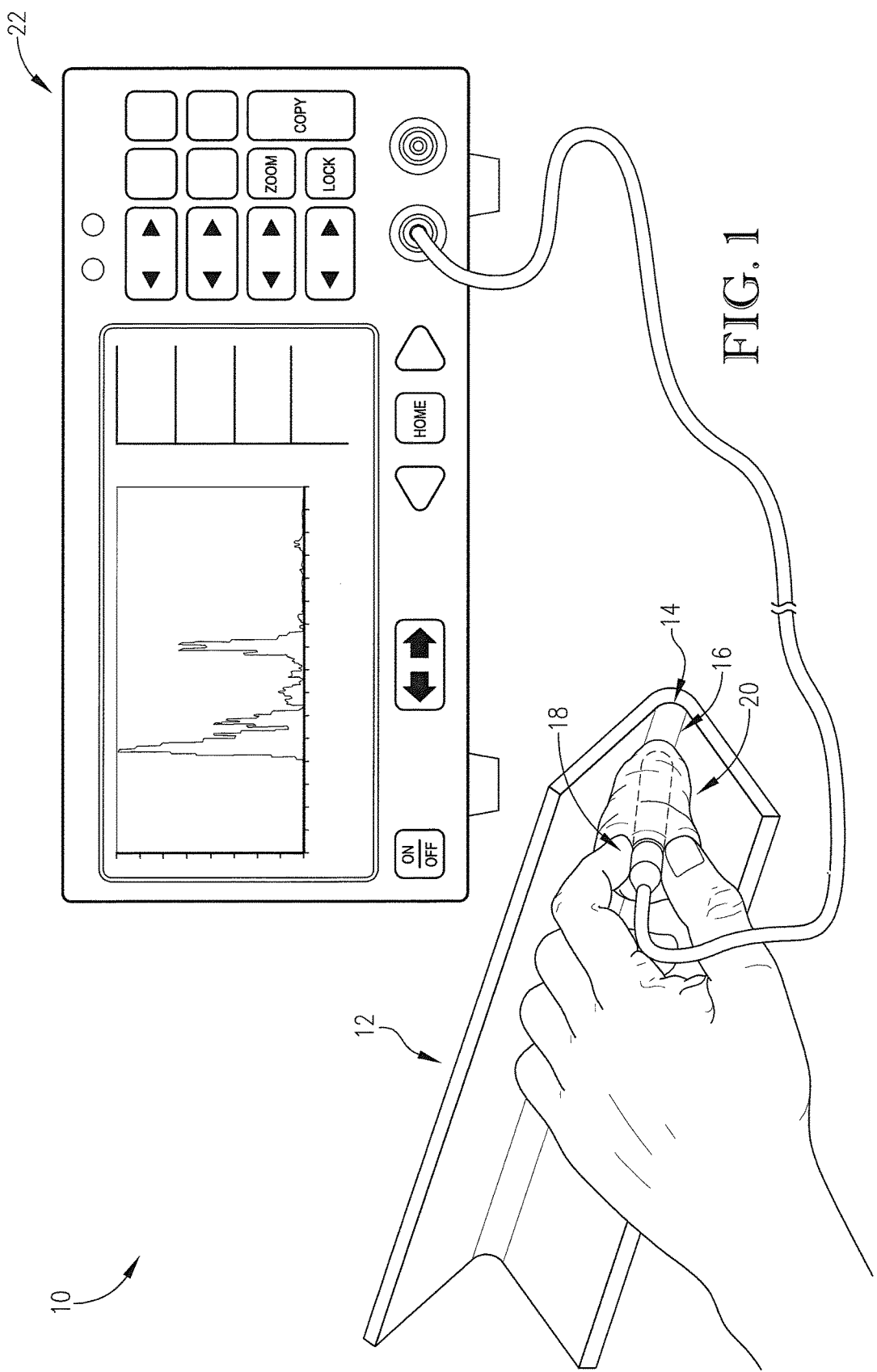
FIG. 1 is a perspective view of a sensor assembly including a remoldable housing, constructed in accordance with an embodiment of the invention.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 2A:
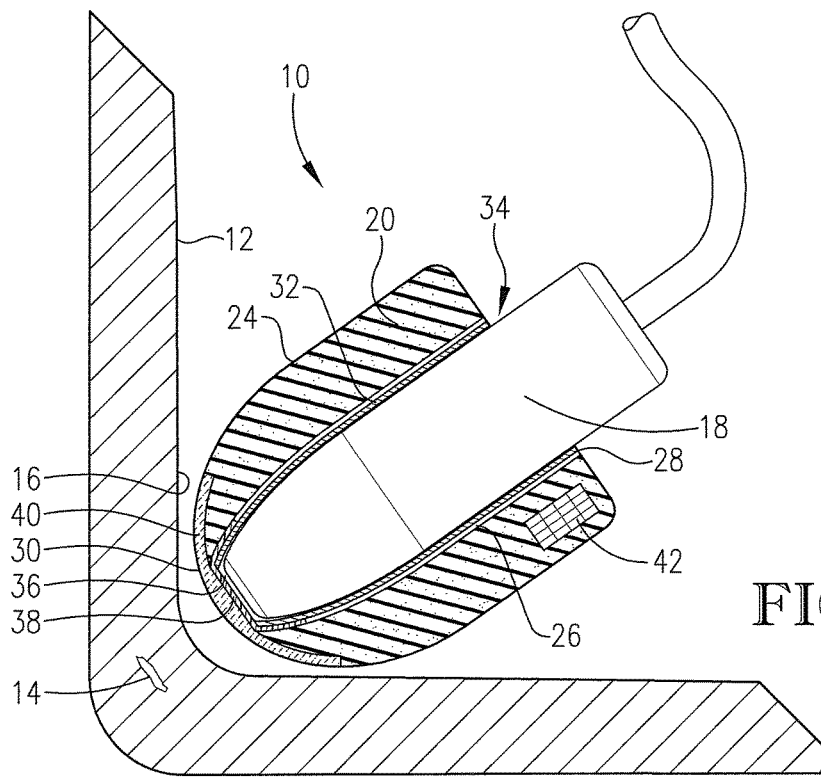
FIG. 2a is a side view of the sensor assembly in FIG. 1 before the housing is molded to conform to the contour of the part.
Figure 2B:
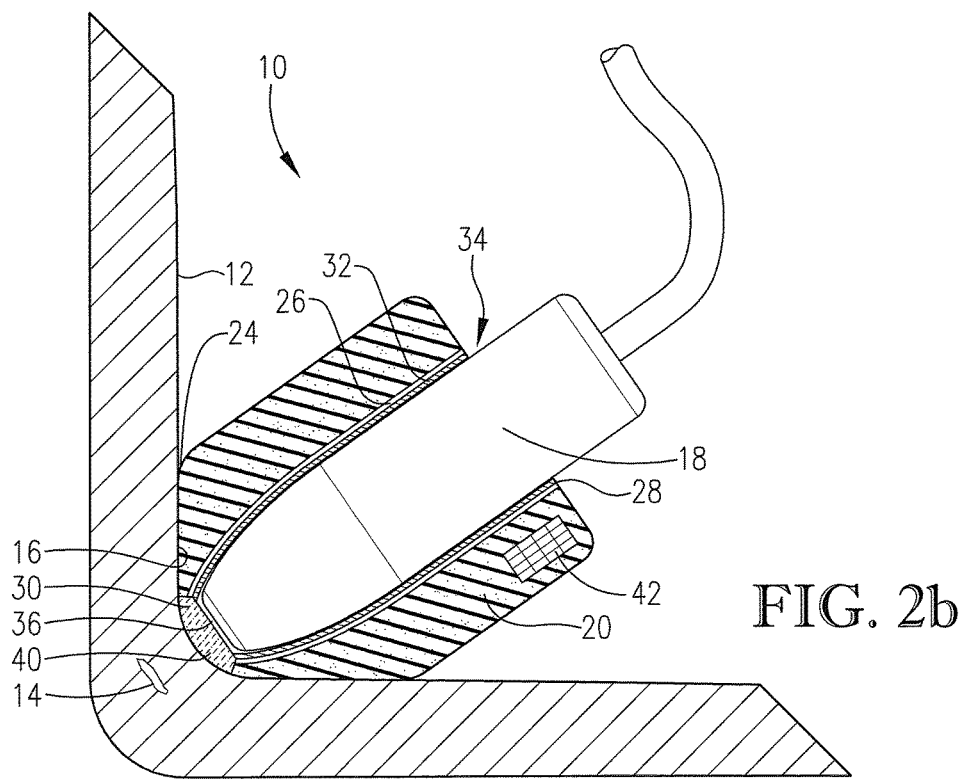
FIG. 2b is a side view of the sensor assembly in FIG. 2a with the housing being molded to conform to the contour of the part.

Turning to the figures, and particularly FIGS. 1-2b, a sensor assembly 10 constructed in accordance with an embodiment of the invention and operable to inspect a part 12 is illustrated. The part 12 may be a piece of raw material, a specimen, a test piece, a manufactured part, a prototype, a finished part, an assembly, an apparatus, or any other object that needs to be inspected. The part 12 may have a defect 14 such as an inclusion, a porosity, a crack, a delamination, or a foreign object that must be detected. The part 12 may also have a contour 16 near the defect 14 that may be used to properly position the sensor 18, as described below. The contour 16 may have an irregularity, a manufacturing defect, a complex shape, or other feature that might make obtaining an optimal or accurate sensor reading difficult.

In one embodiment of the invention, the sensor assembly 10 broadly includes a sensor 18 for sensing the defect 14 and a remoldable housing 20 for retaining and positioning the sensor 18 in alignment with the part 12. The sensor assembly 10 may also include other components such as power supplies, displays, user interfaces, etc. that will not be described in detail herein.

The sensor 18 may be an ultrasonic transducer, a laser, an eddy current probe, a linear array, or any other sensing device. The sensor is operable to transmit a signal to the part 12 and receive the signal or a derivative signal from the part 12. The sensor 18 is communicatively connectible to a processor 22 such as an ultrasonic pulser/receiver, a flaw detector, an A-scan, B-scan, or C-scan instrument, an eddy current instrument, a computer, or any other device capable of creating and/or interpreting the signal or displaying a representation of the signal. Using this signal interpretation, a user can adjust or modify the housing as described below to optimize the signal received, thus ensuring accurate readings. The received signal changes in strength, magnitude, amplitude, intensity, or return time due to the defect 14. For example, if the defect 14 is a delamination, the signal may return earlier than an expected target time. As another example, if the part 12 contains excessive porosity, the signal may return weaker than an expected target strength.

The remoldable housing 20 may be molded to conform to the contour 16 of the part 12, thereby eliminating the need for designing the housing 20 to match the part 12 (FIGS. 2a,b). This also eliminates the need to create and to modify the housing 20 using cumbersome design and manufacturing techniques if the contour 16 of the part 12 is irregular or complex. With the housing 20 being molded to conform to the contour 16, the sensor 18 may be positioned for generating an optimized signal and reading. Its remoldability allows the housing 20 to be used along a portion of the part 12 even if the contour 16 is inconsistent or changes at different points on the portion. The remoldability also allows the housing 20 to be reused on the part 12 or used for multiple parts or multiple contours instead of using a plurality of housings, which may be cumbersome to transport and increases the risk of using the wrong housing.

The remoldable housing 20 is formed of a remoldable material, e.g., thermosetting material such as putty, dough, thermoplastic material or other moldable material such as a shape memory polymer. In one embodiment, the remoldable housing is formed of a shape memory material. Shape memory materials employ reversible shape changing capabilities and may be molded and hardened into multiple shapes. As used herein the term "shape memory material" is defined as any material or composite that exhibits a reversible change in fundamental (i.e., chemical or intrinsic physical) property when subjected to a stimulus, including thermoplastics, shape memory polymers or elastomers, ferrofluids, and alloys. The stimulus is generated by a stimulus source (described below) and may be an electric current, a magnetic field, mechanical stress or loading, a change in pH level, a change in temperature, light, or any other stimulus. Some of the embodiments described herein may use shape memory materials that become moldable when subjected to a sufficient temperature increase and that harden when subjected to a sufficient temperature decrease, but it will be understood that other materials (including non-shape memory materials) may be used instead. The housing 20 may be pre-formed or may be formable from a supply of material, such as thermoplastic or acrylic pellets. The pellets may be combined by squeezing or kneading while heated to form the housing 20. In addition, the housing 20 may include a protective wear resistant outer layer 24 formed of polyethylene, teflon, or other materials suited for sliding contact. The outer layer 24 contacts the part 12 during inspection to protect the housing 20 from receiving abrasions or from being damaged and to prolong the lifespan of the housing 20.

In one embodiment, the housing 20 initially exists in a hard state but becomes moldable when the stimulus is applied to it. For example, a heat stimulus raises an internal temperature of the shape memory material above the material's glass transition temperature $T_g$ (e.g., 150° F.). In this state, some of the molecule structures in the material soften and allow the material to be molded into a different shape. As such, the housing 20 may be molded into a shape that conforms to a contour 16 of the part 12 (FIGS. 2a,b). The temperature may be maintained above $T_g$, and the housing 20 may continue to be molded, until the sensor 18 is at an optimal position for inspecting the part 12. Lowering the internal temperature of the shape memory material below $T_g$ allows the molecule structures to become rigid, which causes the material to harden in its present shape. The temperature may repeatedly be raised above and lowered below $T_g$ without diminution of usability.

The housing 20 may also be pre-formed or moldable to receive at least a portion of the sensor 18. In either case, the housing 20 may be molded to form a cavity 26 for receiving the sensor 18. The cavity 26 conforms to a shape of the sensor 18 for firmly holding the sensor 18 therein. The cavity 26 includes a first end 28 for receiving the sensor 18 therein and optionally includes a second end 30 opposite the first end 28 for allowing the signal to be transmitted or received therethrough. In this case, the cavity 26 extends through the housing 20. Alternatively, the cavity 26 may not include the second end 30 and instead may terminate within the housing 20. In such a case, the signal travels through the housing 20 to the part 12 and returns through the housing 20 to the sensor 18. This may be optimal for the transmission of some ultrasound signals and eddy currents. A sleeve 32 is optionally disposed at least partially in the cavity 26 for receiving the sensor 18, in which case the cavity 26 conforms to a shape of the sleeve 32. The sleeve 32 may be formed of stainless steel, galvanized steel, or other material. The sleeve 32 in turn may have a first opening 34 for receiving the sensor 18 therein and a second opening 36 opposite the first opening 34 for allowing the signal to be transmitted or received therethrough. The second opening 36 may be non-chamfered and may include a thin layer 38 of material such as tape or wrap covering the second opening 36 to prevent the housing material from entering the sleeve 32. The thin layer 38 or a portion thereof that is covering the second opening 36 may be removed once the sleeve 32 is in the cavity 26 so that the signal may be transmitted unimpeded. The housing 20 may also receive a couplant 40 such as an Aquaflex gel, an oil, or other substance between the housing 20 and/or sensor 18 and the part 12. The couplant 40 reduces energy loss by providing a contact between the sensor 18 and the part 12, thus improving the signal.

The stimulus (e.g., heat, electricity, magnetism, mechanical stress) is generated by a stimulus source 42 such as a warm water supply or other warm liquid, an electrical component such as a resistor or a circuit, a stress inducer, or any other stimulus generating device. In one embodiment, the stimulus source 42 is a supply of warm water. The housing 20 or sensor assembly 10 is submersed in the warm water to raise the remoldable material temperature above $T_g$. A cold water supply may optionally be provided to actively lower the remoldable material temperature below $T_g$. In another embodiment, the stimulus source 42 is integrated with the housing 20. For example, the stimulus source 42 may include a flexible heating strip or film that envelopes or surrounds the housing 20. As another example, the stimulus source 42 may be an electrical resistance heater embedded in the housing 20. By integrating the stimulus source 42 with the housing, the stimulus may be applied to the housing 20 without moving the housing 20 away from the part 12. Thus, the sensor 18 may continue to scan the part 12 as the housing 20 is heated. Additional bursts of heat may be applied to the housing 20 as needed while the part 12 is being inspected. For example, if the contour 16 begins to deviate too much to obtain accurate readings, an impulse of heat may be applied from the integrated stimulus source 42 for remolding the part 12 to fit the deviated contour 16.

Figure 3:
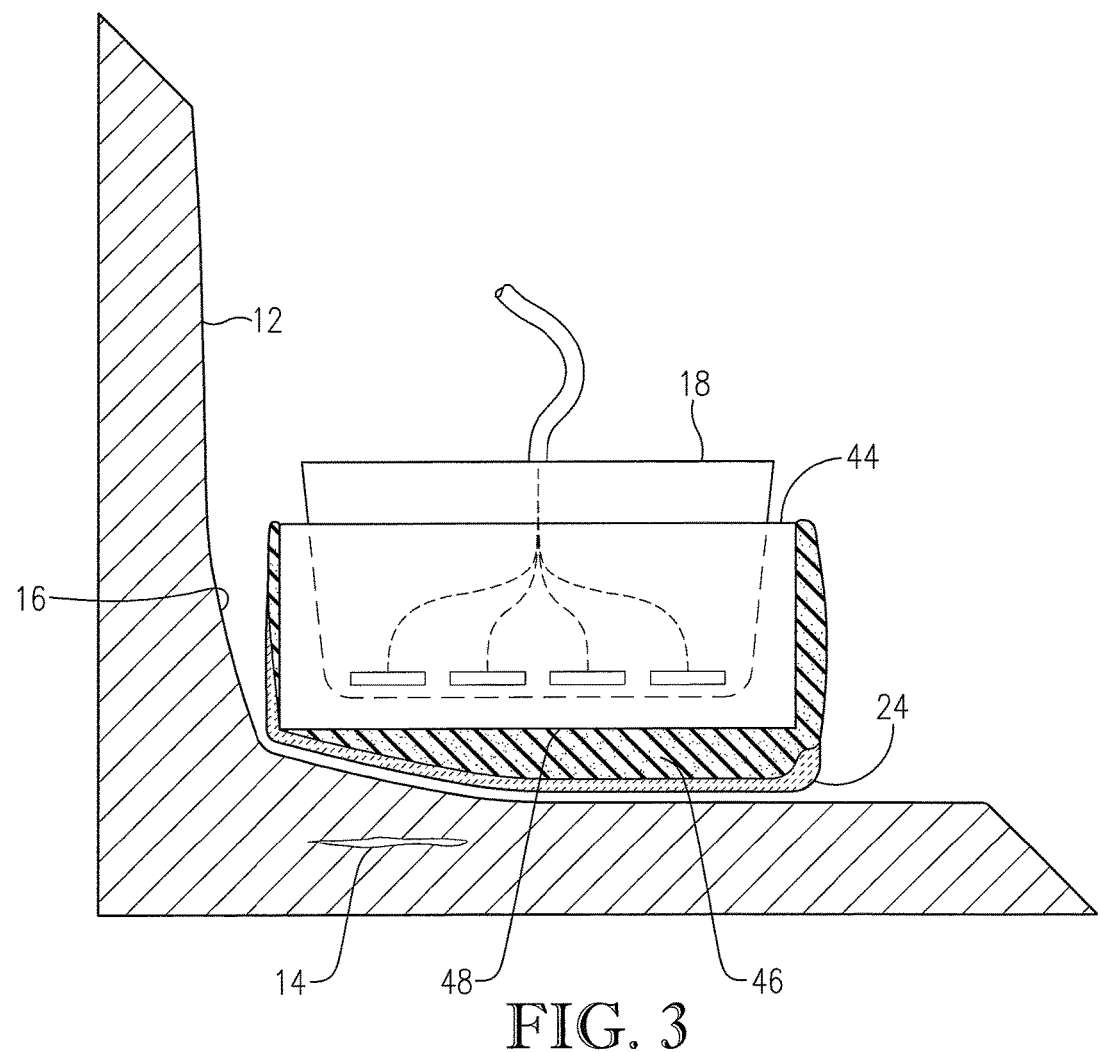
FIG. 3 is a side view of a sensor assembly constructed in accordance with an embodiment of the invention and including a non-remoldable component and a remoldable shim.

In another embodiment of the invention, the sensor assembly 10 includes a sensor 18 (described above) for sensing the defect 14 of the part 12, a non-remoldable component 44 for retaining and positioning the sensor 18 in alignment with the part 12, and a remoldable shim 46 that is operable to be molded into a shape that conforms to the contour 16 when the stimulus is applied thereto (FIG. 3).

The non-remoldable component 44 is a solid block, a shoe, a jig, a mold, etc. that forms an approximation 48 of the contour 16 of the part 12. That is, the non-remoldable component 44 has a shape that generally complements the contour 16. For example, if the contour 16 is a simple step or slope, the component 44 may be a simple cubic block. Thus, sides of the component 44 may generally abut surfaces of the contour 16. Note that the block does not complement the contour 16 exactly. The component 44 may also have a socket, receiver, or other geometry for receiving the sensor 18 therein. The component 44 may allow the sensor 18 to pivot, translate, rotate, or otherwise move with respect thereto. The component 44 may also have protrusions, slots, guides, holes, or other geometries for receiving the remoldable shim 46.

The remoldable shim 46 fills in any space between the component 44 and the contour 16. The shim 46 is formed of a moldable material similar to the remoldable housing 20, described above. In one embodiment, the shim 46 is formed of a shape memory material that becomes moldable when a stimulus (described above) is applied thereto. The shim 46 hardens into the shape when the stimulus is removed. The shim 46 may initially be a sheet or a block of material for being molded to the component 44. The shim 46 is molded into a shape that conforms to the approximation 48 of the component 44 and to the contour 16 of the part 12. Thus, the shim 46 is operable to maintain the sensor alignment when hardened. The shim 46 may have a geometry including a space or gap for allowing the signal to be transmitted therethrough. The shim 46 may include protrusions, slots, guides, holes, or other geometries that are complementary to or interlockable with the protrusions etc. of the component 44. As such, the shim 46 may have a general initial shape that is readily compatible with the component 44. This allows the shim 46 to be easily replaced if the shim 46 becomes damaged or unusable. The shim 46 may be one of a plurality of shims with similar protrusions etc. that are usable with the component 44 such that interchanging the shims entails separating one shim from the component 44 and connecting another shim thereto. Alternatively, the shim 46 may be a permanent element of the component 44. For example, the shim 46 may be housed within the protective outer layer 24, as described above. The outer layer 24 may also be a bladder or other enclosure that is connected to the shim 46. In this way, the shim 46 may be used for multiple parts or multiple portions of the part 12.

In use, the sensor assembly 10 is first assembled. This may include the step of forming the housing 20 or the shim 46 out of a supply of pellets, a sheet, or other material by heating the material to a temperature above $T_g$ and kneading or forming the material into a preliminary shape. Heating the material may involve submersing the material in a supply of warm liquid. Alternatively, an integrated stimulus source 42 may be activated to heat the material. With the material temperature above $T_g$, the housing 20 or shim 46 is kneaded into a shape complementary to the contour 16. The housing 20 may also need to be molded to include the cavity 26. Optionally, the sleeve 32 is inserted into the cavity 26 with the thin layer 38 overlaying the non-chamfered end of the sleeve 32. A portion of the thin layer 38 covering the second opening 36 of the sleeve 32 is removed. The couplant 40 is then inserted into the housing 20, with additional couplant being added as necessary. The sensor 18 is inserted into the cavity 26 or the sleeve 32.

With the sensor 18 in the housing 20 and connected to the processor 22, the housing 20 may be molded to a shape that conforms to the contour 16 and the signal may be optimized. To do this, the housing 20 is placed against the contour 16 with the sensor 18 aimed towards an area of the part 12 to be inspected. The housing 20 is molded until it can be held against the contour 16 without any ancillary movement. The housing 20 is molded until the sensor 18 generates an acceptable or optimized signal. The housing 20 may need to be reheated if its temperature has dropped below $T_g$. Optimizing the signal may require translating, rotating, or pivoting the sensor 18 in one or more directions and molding the housing 20 around the sensor 18. Once the housing 20 is molded correctly and the signal is optimized, the temperature of the housing 20 may be lowered to below $T_g$. The sensor assembly 10 may also be provided partially or fully pre-assembled.

The sensor assembly 10 may then be used to inspect the part 12. To do this, the sensor assembly 10 is moved along the contour 16 such that the sensor 18 moves over the defect 14 while the signal is monitored. If the contour 16 changes significantly, or if the housing 20 encounters an irregularity or an imperfection of the contour 16, the housing 20 may be heated to a temperature above $T_g$ and remolded to fit the contour 16 and to optimize the signal. The temperature is again lowered below $T_g$ to harden the housing 20 into its remolded shape.

If the sensor assembly 10 instead includes the unmoldable component 44 and the shim 46, the following steps are used to inspect the part 12: The sensor 18 is placed in or connected to the unmoldable component 44. The shim 46 is heated to a temperature above $T_g$ and molded to conform to the approximation 48 of the component 44. Alternatively, the shim 46 is attached to the component 44 if the shim 46 is pre-molded to be compatible therewith. The shim 46 is then reheated if necessary and molded to conform to the contour 16. The sensor 18 is then rotated, pivoted, or moved, or the shim 46 is remolded, until the signal is optimized for inspecting the part 12.

To inspect the part 12, the housing 20 is moved along the contour 16 such that the sensor 18 moves over the part 12 while the signal is monitored. If the contour 16 changes significantly, the shim 46 is heated to a temperature above $T_g$ and remolded to fit the contour 16 and to optimize the signal. The temperature is again lowered below $T_g$ to harden the shim 46 into its remolded shape for additional inspection.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A sensor assembly for inspecting a part, the sensor assembly comprising:
    a sensor for sensing a defect of the part;
    a remoldable housing for retaining and positioning the sensor in alignment with the defect of the part, the remoldable housing being formed of a moldable material that is:
        molded into a shape that forms a cavity and conforms to a contour of the part when a stimulus is applied to the remoldable housing, the cavity extending completely through the remoldable housing and having a first end opening for receiving at least a portion of the sleeve and at least a portion of the sensor therein and a second end opening for allowing a sensing signal to pass therethrough; and
        hardened into the shape when the stimulus is removed from the remoldable housing; and
    a sleeve having a first opening for receiving at least a portion of the sensor therein and a second opening for transmitting or receiving the sensing signal therethrough, the sleeve being configurable to be positioned at least partially inside the cavity.

2. The sensor assembly of claim 1, wherein the remoldable housing is configurable to be remolded until the sensor is at an optimal position for sensing the defect.

3. The sensor assembly of claim 1, further comprising:
    a thin layer of material configured to overlay the second opening for preventing the remoldable housing from entering the sleeve when the sleeve is inserted into the cavity, the thin layer of material being configurable to be at least partially removed when the sleeve is at least partially in the cavity.

4. The sensor assembly of claim 1, wherein the second opening is on a non-chamfered end of the sleeve.

5. The sensor assembly of claim 1, wherein the remoldable housing is further configurable to receive a couplant for improving the signal.

6. The sensor assembly of claim 1, further comprising a stimulus source integrated with the remoldable housing, the stimulus source being configurable to apply the stimulus to the remoldable housing.

7. The sensor assembly of claim 6, wherein the stimulus source is embedded in the remoldable housing.

8. The sensor assembly of claim 1, wherein the stimulus is heat.

9. A method for inspecting a part, the method comprising the steps of:
    applying a stimulus to an at least partially remoldable housing;
    molding the at least partially remoldable housing to form a cavity extending completely through the remoldable housing and having a first end opening for receiving at least a portion of a sleeve and at least a portion of a sensor therein and a second end opening for allowing a sensing signal to pass therethrough;
    positioning the sleeve at least partially in the cavity;
    placing the sensor at least partially in the sleeve such that the sensor extends at least partially into the cavity;
    molding the at least partially remoldable housing to conform to a contour of the part such that the sensor is at a position to transmit or receive a signal for sensing a defect of the part;
    detecting the signal;
    remolding the at least partially remoldable housing into a modified shape for repositioning the sleeve and the sensor until an optimized signal is achieved; and
    removing the stimulus to harden the at least partially remoldable housing into the modified shape.

10. The method of claim 9, further comprising the step of forming the at least partially remoldable housing from a supply of shape memory material.

11. The method of claim 9, further comprising the step of:
    remolding the at least partially remoldable housing into a second modified shape when the contour changes to maintain the optimized signal.

12. A sensor assembly for inspecting a part, the sensor assembly comprising:
    a sensor for sensing a defect of the part;
    a remoldable housing for retaining and positioning the sensor in alignment with the defect of the part, the remoldable housing being formed of a moldable material that may:
        be molded into a shape that forms a cavity for receiving at least a portion of the sensor therein and conforms to a contour of the part when a stimulus is applied to the remoldable housing; and
        harden into the shape when the stimulus is removed from the remoldable housing;
    a sleeve having a first opening for receiving at least a portion of the sensor therein and a second opening for allowing a sensing signal to be transmitted or received therethrough, the sleeve being configurable to be positioned at least partially inside the cavity; and
    a thin layer of material configured to overlay the second opening of the sleeve for preventing the remoldable housing from entering the sleeve when the sleeve is inserted into the cavity, the thin layer of material being configurable to be at least partially removed when the sleeve is at least partially in the cavity.

13. A sensor assembly for inspecting a part, the sensor assembly comprising:
    a sensor for sensing a defect of the part;
    a remoldable housing for retaining and positioning the sensor in alignment with the defect of the part, the remoldable housing being formed of a moldable material that may:
        be molded into a shape that forms a cavity and conforms to a contour of the part when a stimulus is applied to the remoldable housing, the cavity extending through the remoldable housing and having a first end for receiving at least a portion of the sensor therein and a second end for allowing a sensing signal to pass therethrough; and harden into the shape when the stimulus is removed from the remoldable housing;

a sleeve having a first opening for receiving at least a portion of the sensor therein and a second opening for transmitting or receiving a sensing signal therethrough, the sleeve being configurable to be positioned at least partially inside the cavity; and a thin layer of material configured to overlay the second opening for preventing the remoldable housing from entering the sleeve when the sleeve is inserted into the cavity, the thin layer of material being configurable to be at least partially removed when the sleeve is at least partially in the cavity.

* * * * *